(12) United States Patent
King et al.

(10) Patent No.: US 10,966,617 B2
(45) Date of Patent: Apr. 6, 2021

(54) HAEMODYNAMIC DATA ESTIMATION

(75) Inventors: David H. King, London (GB);
Mohammed Al-Qaisi, London (GB)

(73) Assignee: Bluedop Medical Ltd., Nottingham (GB)

( * ) Notice: Subject to any disclaimer, the term of this patent is extended or adjusted under 35 U.S.C. 154(b) by 1270 days.

(21) Appl. No.: 13/138,622

(22) PCT Filed: Mar. 11, 2010

(86) PCT No.: PCT/GB2010/000436
§ 371 (c)(1),
(2), (4) Date: Feb. 2, 2012

(87) PCT Pub. No.: WO2010/103277
PCT Pub. Date: Sep. 16, 2010

(65) Prior Publication Data
US 2012/0123246 A1    May 17, 2012

(30) Foreign Application Priority Data
Mar. 13, 2009 (GB) .................... 0904435

(51) Int. Cl.
*A61B 8/00*    (2006.01)
*A61B 5/021*   (2006.01)
(Continued)

(52) U.S. Cl.
CPC .............. *A61B 5/021* (2013.01); *A61B 5/026* (2013.01); *A61B 5/02007* (2013.01);
(Continued)

(58) Field of Classification Search
None
See application file for complete search history.

(56) References Cited

U.S. PATENT DOCUMENTS 5,409,010 A    4/1995  Beach et al.
6,007,491 A *  12/1999 Ling et al. .................. 600/481
(Continued)

FOREIGN PATENT DOCUMENTS

EP          1715428      10/2006
WO    WO 2001/021057    3/2001
(Continued)

OTHER PUBLICATIONS

Bohorquez et al., "An Integrated-Circuit Switched Capacitor Model and Implementation of the Heart", Oct. 2008, pp. 1-5.*
(Continued)

*Primary Examiner* — Christopher L Cook
(74) *Attorney, Agent, or Firm* — Patent Capital Group

(57) ABSTRACT

Techniques exist for measuring local blood velocity of flow rate waveforms in, for example, mammalian vascular segments. A method and system for deriving information on disease in vascular segments, for example mean pressure, drop in mean pressure and/or hydraulic resistance, from such measured waveforms is described. The waveforms can, for example, be measured non-invasively using Doppler ultrasound or magnetic resonance techniques. Form factors (Vff, Pff) for the velocity waveform and the central arterial pressure are determined. Stenosis may be detected by detecting changes e.g in Vff/Pff.

31 Claims, 6 Drawing Sheets

(51) Int. Cl.
    A61B 5/026    (2006.01)
    G01R 33/563   (2006.01)
    A61B 5/02     (2006.01)
    A61B 8/06     (2006.01)
    A61B 5/022    (2006.01)
(52) U.S. Cl.
    CPC ........ *G01R 33/56308* (2013.01); *A61B 5/022* (2013.01); *A61B 5/0263* (2013.01); *A61B 8/06* (2013.01); *A61B 8/4245* (2013.01)

(56)  References Cited

U.S. PATENT DOCUMENTS

| | | | |
|---|---|---|---|
| 6,251,077 B1 | 6/2001 | Mo et al. | |
| 2005/0119569 A1* | 6/2005 | Ohtake | 600/437 |
| 2005/0137479 A1* | 6/2005 | Haider | 600/440 |
| 2005/0156593 A1* | 7/2005 | Assmann et al. | 324/306 |
| 2007/0123779 A1* | 5/2007 | Hoctor | A61B 5/02125 600/438 |
| 2007/0293760 A1* | 12/2007 | Schaafsma | 600/454 |
| 2008/0027330 A1* | 1/2008 | Naghavi et al. | 600/481 |
| 2008/0114255 A1 | 5/2008 | Schwartz et al. | |
| 2009/0088626 A1* | 4/2009 | Sutton et al. | 600/419 |
| 2010/0081941 A1* | 4/2010 | Naghavi | A61B 5/015 600/481 |
| 2010/0198062 A1* | 8/2010 | Everett et al. | 600/437 |
| 2010/0331688 A1 | 12/2010 | Baba | |
| 2013/0281862 A1 | 10/2013 | Yoon et al. | |
| 2014/0358000 A1 | 12/2014 | Gupta et al. | |
| 2017/0181642 A1 | 6/2017 | King et al. | |

FOREIGN PATENT DOCUMENTS

| | | |
|---|---|---|
| WO | 2007012809 A2 | 2/2007 |
| WO | 2007056386 A2 | 5/2007 |
| WO | 2019135096 A1 | 7/2019 |

OTHER PUBLICATIONS

Nakayama et al., "Ascending fractional pulse pressure closely relating to large artery function", Journal of Human Hypertension, 2002.*

Formaggia et al., "The Circulatory system: from case studies to mathematical modeling", 2006, avilable online at http://link.springer.com/chapter/10.1007%2F88-470-0396-2_7.*

R. Nave, "Current Law and Flowrate", Available online Jan. 26, 2000, Wayback Screen shot Feb. 19, 2008, http://hyperphysics.phy-astr.gsu.edu/hbase/electric/watcir2.html.*

Huppert et al., "A multicompartment vascular model for inferring baseline and functional changes in cerebral oxygen metabolism and arterial dilation", Journal of cerebral Blood flow and metabolism, 2007.*

Evans et al., "The Relationship between Ultrasonic Pulsatility Index and Proximal Arterial Stenosis in a Canine Model", Apr. 1980.*

Post Exercise Doppler Blood Velocity Patterns in Health and Disease; D.H. King et al., published more than 1 year prior to the priority date of the present application (2 pages).

Grundlagen der Dynamic des Arterienpulses, Wetterer E and Kenner Th, Springer-Verlag, Berlin, 1968; Chapter 8: Incident and incoming waves (translated from the German text) (8 pages).

Pressure-Flow Characteristics of Coronary Stenoses in Unsedated Dogs at Rest and during Coronary Vasodilation; K. Lance Gould; Circulation Research: vol. 43, No. 2, pp. 242-253, Aug. 1978 (12 pages).

An in vivo study of the total occlusion method for the analysis of forward and backward pressure waves; D.L. Newman et al.; Cardiovascular Research, 1979, 13, pp. 595-600 (6 pages).

Strategies for Rapid NMR Rheometry by Magnetic Resonance Imaging Velocimetry; Stephen J. Gibbs et al.; Journal of Magnetic Resonance 125, pp. 43-51, 1997 (9 pages).

Real-Time Volumetric Flow Measurements With Complex-Difference MRI; Richard B. Thompson et al.; NIH Public Access, Author Manuscript; Magn Reson Med. Dec. 2003; 50(6): 1248-1255; pp. 1-15 (15 pages).

Online Viscosity Measurement of Complex Solutions Using Ultrasound Doppler Velocimetry; Volkan Koeseli et al.; Turk J Chem, 30 (2006), pp. 297-304 (8 pages).

PCT International Search Report and Written Opinion in PCT International Application Serial No. PCT/GB2010/000436 dated Jun. 10, 2010.

PCT International Preliminary Report on Patentability in PCT International Application Serial No. PCT/GB2010/000436 dated Sep. 13, 2011.

Dan Dan et al: "Cerebral blood flow velocity declines before arterial pressure in patients with orthostatic vasovagal presyncope." Journal of the American College of Cardiology, vol. 39, No. 6, Mar. 20, 2002 (Mar. 20, 2002) , pp. 1039-1045, XP002583383 ISSN: 0735-1097 p. 1039-p. 1040.

Leotta et al: "Display of spatially-registered Doppler spectral waveforms and three-dimensional vein graft geometry" Ultrasound in Medicine and Biology, vol. 31, No. 10, Oct. 1, 2005 (Oct. 1, 2005), pp. 1317-1326, XP005150232 ISSN: 0301-5629.

De Morais Filho et al: "Segmental Waveform Analysis in the Diagnosis of Peripheral Arterial Occlusive Diseases" Annals of Vascular Surgery, vol. 18, No. 6, Nov. 1, 2004 (Nov. 1, 2004), pp. 714-724, XP005941303 ISSN: 0890-5096 the whole document.

Hong Gi Li, et al., "Fourier Transformation of Arterial Doppler Waveforms of the Lower Extremity," Journal of Clinical Ultrasound, vol. 32, No. 6, Jul./Aug. 2004 (pp. 277-285).

Buyens et al., "Calculation of Left Ventricle Relative Pressure Distribution in MRI using Acceleration Data", Magnetic Resonance in Medicine (Year: 2005).

Dan et al., "Cerebral Blood Flow Velocity Declines Before Arterial Pressure in Patients with Orthostatic Vasovagal Presyncope", J. American College of Cardiology (Year: 2002).

Nakayama et al., "Ascending fractional pulse pressure closely relating to large artery function", J. of Human Hypertension (Year: 2002).

Sesso et al. "Systolic and Diastolic Blood Pressure, Pulse Pressure and Mean Arterial Pressure as predictors of Cardiovascular Disease Risk in Men", Hypertension (Year: 2000).

USPTO Non-Final Office Action in U.S. Appl. No. 15/403,760 dated Sep. 15, 2020, 19 pages.

EPO Communication pursuant to Rules 161 issued for EP Application No. 18708730.9 dated Sep. 11, 2020; 3 pages.

International Preliminary Report on Patentability issue in PCT Application No. PCT/IB2018/000047 dated Jul. 7, 2020, 7 pages.

International Search Report and Written Opinion issued in PCT Application No. PCT/IB2018/000047 dated Sep. 12, 2018; 11 pages.

Scheinfeld et al., "Understanding the Spectral Doppler Waveform of the Hepatic Veins in Health and Disease," RadioGraphics 2009, vol. 29, No. 7, pp. 2081-2099.

Tehan et al., "Use of hand-held Doppler ultrasound examination by podiatrists: a reliability study," Journal of Foot and Ankle Research, 2015, 7 pages.

USPTO Final Office Action in U.S. Appl. No. 15/353,862 dated Dec. 23, 2020, 15 pages.

USPTO Non-Final Office Action in U.S. Appl. No. 15/353,862 dated Mar. 27, 2020, 14 pages.

Wennberg, "Approach to the Patient with Peripheral Arterial Disease", American Heart Association, downloaded from http://ahajournals.org on Mar. 23, 2020, 10 pages.

\* cited by examiner

HAEMODYNAMIC DATA ESTIMATION

FIELD OF THE INVENTION

The present invention relates to a system and method for estimating haemodynamic data, in particular although not exclusively to non-invasively obtaining in vivo mean pressure, mean pressure drop and/or hydraulic resistance data from within the normal and diseased segments of, in particular, the intact mammalian vascular system, human or animal.

BACKGROUND OF THE INVENTION

With human life expectancy increasing world wide the effects of progressive arterial disease become more apparent within the ageing population. This disease commonly takes the form of stenoses (localised cross sectional arterial narrowing) which may represent a significant resistance to blood flow in, for instance, the coronary arteries, the iliac and femoral arteries and the internal carotid arteries, resulting in angina or claudication or stroke. The effect of a stenosis on resistance is non linear, causing symptoms when narrowing exceeds a threshold value.

Where narrowing completely obscures the arterial cross section the stenosis becomes an occlusion. In this case smaller calibre arteries (collateral) direct blood flow past the occlusion, often rejoining the original arterial pathway downstream of the occlusion. In effect the collateral pathway can be modelled as a special case of a stenosis. It should be noted that collateral flow also starts to develop around a stenosis as the lumen becomes more obscured. In what follows a stenosis or an occlusion will be used interchangeably where permitted by the context and will be referred to collectively as 'disease' or 'a lesion'.

In order to gauge the clinical significance of individual lesions, local haemodynamic information needs to be obtained.

Ultrasound based Doppler shift spectral analysis and imaging techniques using Continuous Wave Doppler and Duplex scanning machines allow velocity and (in the latter case) flow rate data to be directly measured non-invasively in many accessible parts of the vascular network. Similarly, techniques exist for calculating blood velocity and flow rates from Magnetic Resonant Imaging (MRI) data (see 'Real-time volumetric flow measurements with complex-difference MRI' Thompson R B and McVeigh E R in Magnetic Resonance in Medicine Vol 50, Issue 6, Pages 1248-1255, herewith incorporated by reference herein). MRI data can be obtained from all parts of the vascular network, some of which are inaccessible to ultrasound scanners.

The ability to establish the magnitude of stenoses by measuring increased peak velocity within the stenosis has proved to be valuable clinically. This is, however, not applicable to an occlusion. Blood flow rate either through a stenosis or around an occlusion has been less useful clinically because the vascular bed changes its characteristics dynamically by vasodilating and vasoconstricting under active and passive control, in order to allow optimum blood flow and pressure to perfuse the major organs and muscle beds when required. This is in effect a physiological servo system which has the effect of reducing the influence of a lesion's resistance on blood flow.

Downstream blood pressure and pressure drop across a lesion have been shown to be sensitive indicators of stenotic disease but prior to the present invention this could only be assessed in the limbs, either employing occlusive cuff or servo controlled cuff based methods or elsewhere in the vascular system by invasive insertion of pressure catheters directly into the vascular system.

It would be desirable to derive a direct measure of disease magnitude, one which is resistance based, computed from local blood flow and pressure data. The hydraulic resistance of a lesion is relatively independent of the state of the vascular load, be it vasoconstricted or vasodilated, and is able give a precise estimate of disease magnitude. Prior to the present invention, the non invasive computation of 'in vivo' absolute mean arterial pressure and/or absolute hydraulic resistance of a lesion or a series of lesions, has not been practical except in the case of single isolated lesions under ideal conditions. This is often not the case because each lesion is individual and depending (for instance) on the degree of flow separation at the diverging end of a stenosis, possesses a widely varying, non linear, flow dependent hydraulic resistance characteristic which may be either difficult, impractical or impossible to predict (for instance) by employing well known equations such as those described by Poiseulle or by Bernoulli (see 'Pressure-Flow characteristics of coronary stenoses in unsedated dogs at rest and during coronary vasodilation', Gould K L, Circulation Research Vol 43, No 2, August 1978, herewith incorporated by reference herein). Significantly, a large proportion of haemodynamically significant lesions have become total occlusions by the time the symptoms have caused a patient to seek medical advice. Prior to this invention the combined effect of complex collateral circulation bypassing such an occlusion has not been amenable to analysis by conventional formulae.

SUMMARY OF THE INVENTION

Embodiments of the present invention provide a system and method for deriving information or data on a lesion based on a form factor of wave forms derived non-invasively using measured physiological data such as blood velocity or flow rates and pressure supplying a specific vascular bed, that is the vascular vessels and tissues of an organ or muscle), under examination. These embodiments are based on the realisation that simple form factor measures extracted from measured velocity or flow rate and pressure data can be used to 1. Estimate ratio between upstream and downstream resistance pertaining to a specific measurement location/vascular bed (eg brain, kidney, muscle).
2. Estimate local absolute mean blood pressure perfusing that vascular bed.
3. Identify the maximal vasodilation associated with a specific vascular bed in disease and normality.

And in the case that local bloodflow can be measured:

5. Absolute upstream and downstream resistances can be calculated.
6. Absolute resistance of specific lesions can be calculated and mapped.
7. The effect of removal of a specific lesion (eg by balloon angioplasty) on maximal bloodflow to a specific vascular bed can be estimated.
8. The unit length resistance (linear resistance) of a blood vessel can be calculated.

In some embodiments, these calculations include an estimation of (central) mean arterial pressure and an estimate of a measure of pulsatility of central blood pressure estimated using a cuff, stethoscope and sphygomomanometer, for example for a brachial measurement. The velocity or flow data can be measured in a variety of ways and embodiments include a CW Doppler device for velocity measurements or a Duplex ultrasound or Multi Gate Doppler ultrasound device for velocity and/or flow rate measurement. By measuring or estimating incident blood pressure and local blood flow rate non-invasively at selected points in the vascular bed, the magnitude of the increased haemodynamic resistances due to a lesion can be calculated and mapped and changes in resistances and other measures can be used to pinpoint the location of a stenosis.

Embodiments of the invention use these measures to derive haemodynamic data indicative of the presence or absence of a lesion, and/or indicative of a response of a healthy vascular system to stimuli such as drug infusion, over breathing, $CO_2$, $O_2$, respiratory disease, cardiac failure, ambient temperature, digestion or mental arithmetic.

In some embodiments an estimate may be made of the mean pressure drop between any two points on a blood vessel, separated by a known linear distance. When combined with mean blood flow data the haemodynamic resistance per unit length of blood vessel may be computed. This measure is known as linear resistance and such measures may be compared with established norms for specific blood vessels. Arising from this capability further measures may be derived. For instance fluid (blood) viscosity may be derived by combining measures of shear stress divided by shear strain. The foregoing provides shear stress data, whilst shear strain can be derived from fluid (blood) velocity profiles obtained from within the blood vessel. To this end instantaneous blood velocity profile data may be derived from a Multi Gate Doppler or MRI device which then provides detailed information on a whole range of shear rates ranging (typically) between a maximum at the vessel wall and a minimum along the vessel axis. (See 'Online viscosity measurement of complex solutions using Ultrasound Doppler Velocimetry', Koseli V, Zeybek S and Uludag Y: Turk J Chem 30 (2006), 297-305 herewith incorporated by reference herein). Also (see 'Strategies for rapid NMR rheometry by Magnetic Resonance Image Velocimetry' Gibbs S J, Haycock D E, Frith N J, Ablett S and Hall L D, J of Magnetic Resonance 125, 43-51 (1997) herewith incorporated by reference herein)

In some embodiments, measurements from different points of the body are correlated with a corresponding video image to display a map of peripheral pressure or resistance overlaid over a video image of a patient. In some embodiments, velocity or flow data is derived using a MRI scanner, allowing calculated pressure or resistance data to be displayed as a colour coded vascular pressure or resistance map overlaid over a corresponding structural image derived by the MRI scanner. The embodiments are particularly suited to measurements in mammals both non-human and human.

Embodiments of the invention are now described by way of example only and with reference to the accompanying drawing in which.

DETAILED DESCRIPTION OF AN EMBODIMENT OF THE PRESENT INVENTION

Figure 1:
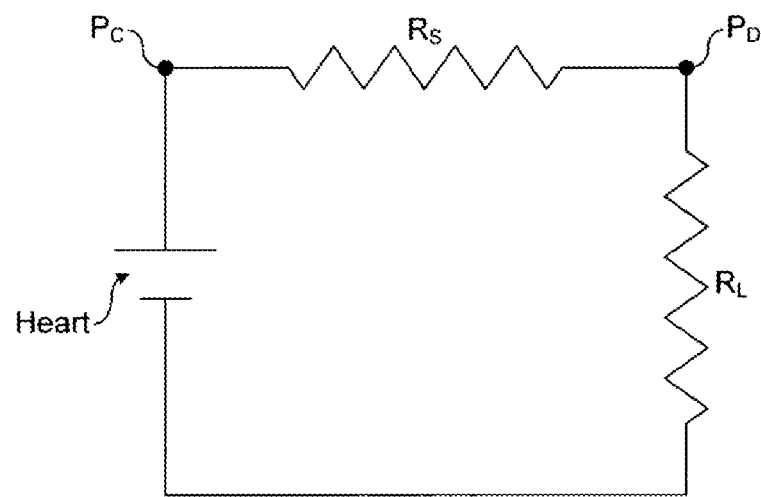
FIG. 1 illustrates a haemodynamic model informing the present invention.

With reference to FIG. 1, a simplified haemodynamic model of a mammalian vascular system comprises a driving element corresponding to the heart, a source resistance $R_S$ corresponding to the internal resistance of the heart and the resistance of the transit arteries carrying blood to the vascular beds, a vascular segment or segment of vasculature represented by the load resistance $R_L$ which also includes the resistance of the veins closing the circuit to the heart. The heart generates a variable flow rate at a constant pressure $P_C$, which flows through the transit arteries represented by $R_S$. This generates a pressure drop across $R_S$, finally perfusing the vascular bed at a pressure $P_D$. The venous component of the resistance and pressure drop across RL is small under physiological conditions (with the central venous pressure being much lower than the central and peripheral applied pressures, the former being of the order of less than 10 mmHg and the latter being of the order of 100 mmHg). The pressure $P_D$ and resistance $R_L$ can therefore, to a first approximation, be taken as being characteristic of the peripheral bed under investigation. It should be noted that in the case of an arterio-venous fistula created for dialysis the venous side becomes arterialised and in this special case the return pathway via superficial vein to deep vein can be considered as the arterial supply in the model described below. The Right Heart reference pressure (Central Venous Pressure) is normally close to zero with reference to ambient atmospheric pressure. Where the Right Heart reference pressure becomes abnormally elevated due to pathology, the accuracy of the algorithm will be reduced proportionately because the magnitude of the effective driving pressure/time waveform will be correspondingly reduced. A correction can be made if Central Venous Pressure is known or can be estimated. (see below)

In analogy with an electric voltage divider circuit, the distal mean pressure $P_D$ is related to the central mean pressure $P_c$ by $$PD=PC/(1+R_S/R_L) \qquad \text{equation 1}$$

where RS is the internal heart and transit artery resistance and RL is the vascular bed resistance of the tissue under investigation, both in peripheral resistance units (PRU) or their clinically accepted equivalent. PRU is usually defined in terms of mmHg/ml per second. Pressures are in units of mmHg.

It can thus be seen that, based on a simple haemodynamic pressure divider model, peripheral pressure can be calculated from central pressure, if both the source and load resistances are known or can be measured. However, it is precisely the lack of knowledge of these quantities, which is one aspect of the problems addressed by embodiments described herein.

It has previously be shown that, in the matched state when by definition $R_S=R_L$, the incident pressure and resultant velocity waveforms in a circuit similar to the one shown in FIG. 1 are of the same shape and not distorted because any capacitive and inductive effects (arterial compliance and blood mass in this analogue) are eliminated (see Grundlagen der Dynamic des Arterienpulses, Wetterer E and Kenneth Th, Springer-Verlag Berlin, 1968). In this matched state, the ratio $R_S/R_L$ used in the calculation of $P_D$ above is unity.

Underlying the described embodiments, is the realisation that given the similarity of flow and pressure waveforms shown previously, the ratio of a form factor descriptive of the shape of the pressure and velocity waveforms should equally be unity and that it may be possible to generalise this correspondence between a ratio of resistances and a ratio of form factors across a range of resistances outside the matched state to provide a measurable quantity which can be used to estimate peripheral or distal pressure ($P_D$) at any point around the vascular circuit from the left side of the heart (arterial) to the right side (venous).

Figure 2:
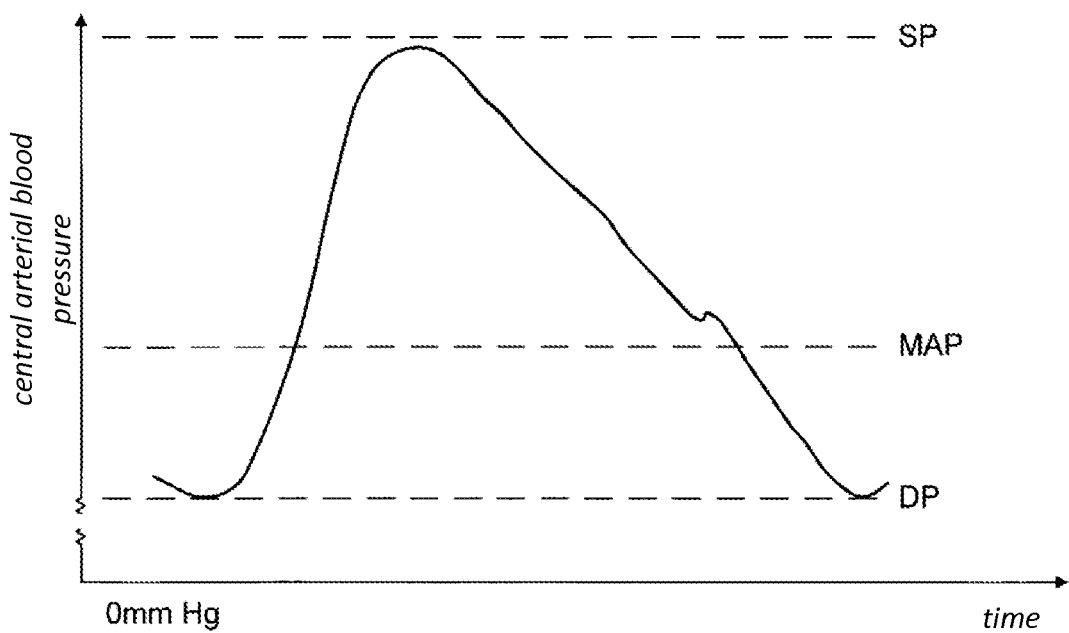
FIG. 2 illustrates an example central arterial blood pressure/time waveform including AC and DC terms.

One Form Factor describing the AC term of the pressure waveform relative to the DC level is the ratio of the pulse pressure (systolic or peak pressure minus diastolic or lowest pressure) relative to the mean pressure, averaged over one heart beat. A central arterial pressure wave is shown in FIG. 2, illustrating Systolic Pressure (SP), Mean Arterial Pressure (MAP) and Diastolic Pressure (DP) and the zero pressure reference datum. In the matched state, the velocity/time and pressure/time waveform will be of the same shape. In the present description, the Form Factor (ff) for the central arterial pressure is termed Pressure form factor ($P_{ff}$), such that $P_{ff}=(SP-DP)/MAP$ and the form factor for the velocity waveforms measured in the periphery is termed Velocity form factor ($V_{ff}$), such that $V_{ff}=(Vmax-Vmin)/V$ mean. It should be noted that the flow/time waveform will be identical in shape to the velocity/time waveform. Therefore the argument (below) applies to a corresponding flow/time form factor ($F_{ff}$) calculated from a flow/time waveform, as well. In the remainder, a reference to $V_{ff}$ is understood to include reference to $F_{ff}$, context permitting.

In the matched state, because the pressure/time and velocity/time waveform shapes are identical, the ratio of their form factors will be identical. Thus $P_{ff}/V_{ff}=1$. But $R_S/R_L=1$ in the matched state so that by substituting either $R_S/R_L$ or $P_{ff}/V_{ff}$ in equation 1, the identical result is obtained such that $P_D=P_C/2$.

Underlying the described embodiments is the realisation that this relationship may hold not only in the matched states but generally. Examining an upper limit for the distal pressure when $R_L$ is infinite under total peripheral vasoconstriction, $R_S/R_L=0$. In this state the DC velocity (flow) term approaches zero and therefore $V_{ff}$ also approaches infinity, thus $P_{ff}/V_{ff}$ approaches 0. Substituting, $R_S/R_L$ or $P_{ff}/V_{ff}$ in equation 1, the identical result is obtained such that $P_D$ approaches $P_C$.

Similarly, when the peripheral bed is bypassed, for example with an a-v fistula as used in dialysis, $R_L$ approaches zero and therefore $R_S/R_L$ approaches ∞. Similarly Vff approaches zero because the DC velocity component becomes very much larger than the AC component of the velocity/time waveform. Therefore $P_{ff}/V_{ff}$ approaches ∞. Substituting either $R_S/R_L$ or $P_{ff}/V_{ff}$ in equation 1, the identical result is obtained such that PD approaches 0.

The above theoretical considerations show that at 3 points over the range from peripheral bed bypass to total peripheral vasoconstriction, with the matched state occurring in between these two, the ratio $R_S/R_L$ can be replaced with a ratio of form factors as $P_{ff}/V_{ff}$. This suggests the following formula for calculating $P_D$:

$$P_D=P_C/(1+P_{ff}/Vff) \qquad \text{equation 2}$$

Similarly, the pressure drop between the source and the load is given by:

$$P_C-P_D=PC/(1+V_{ff}/P_{ff}) \qquad \text{equation 3}$$

in accordance with the voltage divider analogy.

A number of assumptions underlie the derivation of the above relationship, which are now listed in as much as they have not been discussed above:

1) $P_{ff}$ and $V_{ff}$ are always finite.
2) Pff brachial pressure=Pff central pressure=$P_{ff}$ incident pressure. The validity of the second assumption can be tested in a number of ways (see below).
3) The subject is supine. Otherwise any difference in hydrostatic pressure between the measurement of central blood pressure (e.g. using a brachial cuff) and the measurement of the velocity waveform can be taken account of by a correction of $\Delta P=(h[\text{centimetre}]/13.6)$ [mmHg] where h is the vertical distance between centre cuff and the velocity or flow measurement location, such for locations below the cuff:—

$$P_D(\text{corrected})=P_D \text{ calculated}+\Delta P$$

4) The incident pressure originates from the left ventricle. If this is not the case, for example for measurements involving the right ventricle and the pulmonary circulation, the incident blood pressure waveform could be calculated from direct measurements employing a catheter based pressure transducer. Only one determination would normally be made since this value is assumed to be a constant except in exceptional circumstances.
5) If an elevated Central Venous Pressure (CVP) is present and known, a correction can be carried out such that CVP is subtracted from Mean Arterial Pressure when calculating Pff such that:

$$P_{ff}=SP-DP/(\text{Mean Arterial Pressure}-CVP)$$

6) Arterial characteristics are assumed to be constant over a heart beat. This does not apply to coronary arteries where the dynamic change of the transit arteries and vascular bed due to mechanical compression during the systolic ejection period (SEP), transiently increases the resistance of the vascular bed (myocardium). However, as long as $P_{ff}$ and Vff or $F_{ff}$ are computed only for the non compressed, diastolic part of the cardiac cycle, the same equations should be applicable.
7) Where estimation of the perfusion pressure supplied to a specific organ (eg kidney, brain), the model described above assumes that the waveform underlying the calculation of $V_{ff}$ is measured at the termination of the supply to the vascular bed under test.

Figure 3A:
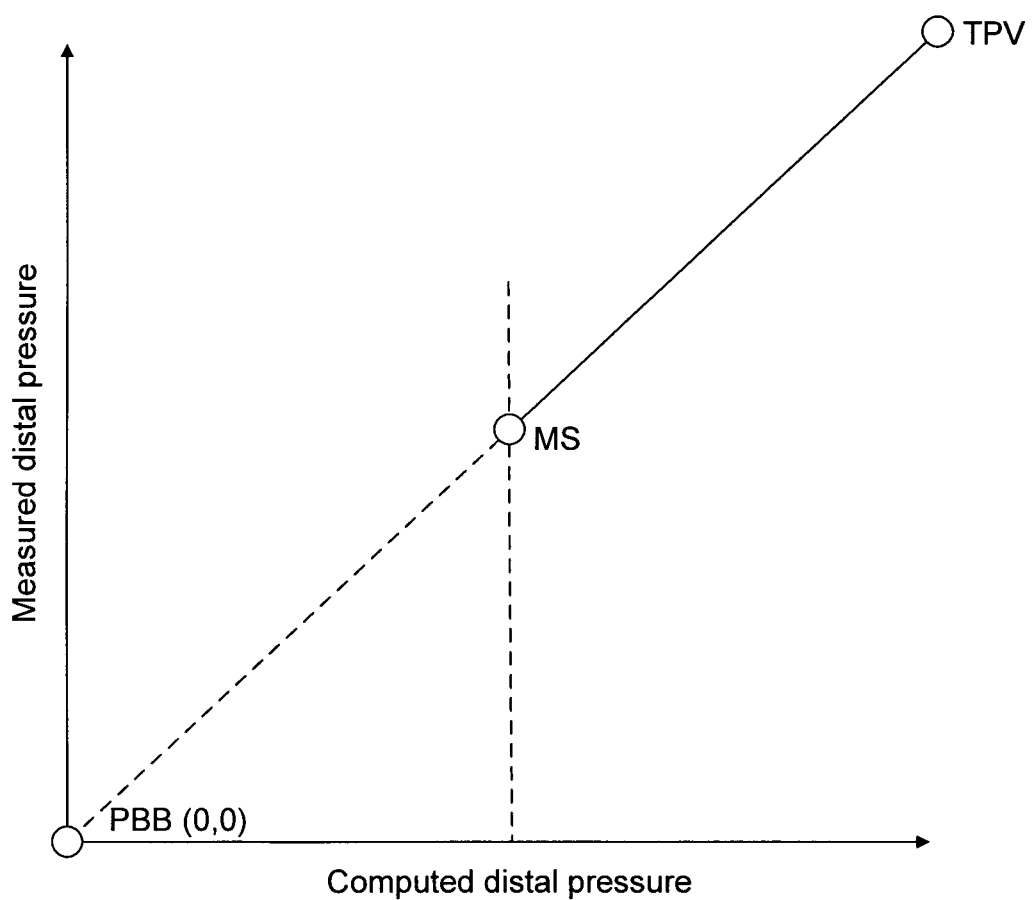
FIG. 3A illustrates a relationship between measured distal mean pressure and distal mean pressure computed in accordance with described embodiments.

The above discussion of an expression for calculating peripheral pressure based on mean central pressure and a ratio of measures of shape of central pressure and peripheral velocity waveforms has been based on a theoretical analysis of the behaviour of these quantities at Total Peripheral Vasoconstriction (TPV), the Matched State (MS) and Peripheral Bed Bypass (PBB). The result is further supported by experimental data now described with reference to FIG. 3A. FIG. 3A schematically depicts experimental data obtained from canine experiments plotting computed distal pressure based on the expression described above against measured distal pressure, together with the PBB, MS and TPV states discussed above. Experimental data was only obtained between the MS and TPV regimes but a straight line fit to that data indicates that the relationship between the measured distal pressure and computed distal pressure has a slope of one and a y intercept approaching the origin, as can be expected based on the above theoretical discussion.

Experimental validation of the described method for calculating pressure from velocity of flow waveforms was obtained by inserting pressure sensitive catheters (having side-facing pressure sensors) into the abdominal aorta and femoral artery of an anesthetized fifteen kilogram greyhound. Additionally, a directional Doppler Ultrasound pencil transducer was clamped directly over the surgically exposed femoral artery allowing Doppler Velocity Spectral data to be recorded. An electromagnetic cuff type blood flow transducer was positioned around the femoral artery, adjacent to the Doppler probe allowing instantaneous calibrated bloodflow to be recorded. A pressure/time waveform was obtained from the Abdominal Aorta allowing heartbeat to heartbeat measurements of SP, DP, mean aortic blood pressure, Pc and $P_{ff}$. Concurrently the pressure/time waveform was recorded from the femoral artery allowing synchronous beat to beat measurements of $P_D$. Simultaneously a blood velocity/time spectral waveform obtained from the femoral artery Doppler probe, yielded beat to beat measurement of $V_{ff}$. Rs and $R_L$ for each heartbeat were also calculated from direct measurements of synchronously recorded aortic pressure Pc, femoral artery pressure $P_D$ and calibrated femoral artery bloodflow rate.

Two experiments were carried out, whilst recording the parameters described above. Experiment 1 recorded the dynamic hyperaemic response immediately after a 1 minute iliac artery compression involving complete cessation of bloodflow through the artery. Upon releasing the compression a range of $P_D$ values was recorded whilst bloodflow peaked and subsequently stabilised into the resting state. Experiment 2 was carried out in the resting arterial state and recorded the dynamic responses during partial, varying manual compression of the iliac artery. This yielded a similar range of $P_D$ values to the first experiment. $P_{ff}$, $V_{ff}$, $P_C$ and $P_D$ were recorded for each cardiac cycle. The pressure data was corrected for the estimated hydrostatic height difference between pressure sensors.

Figure 3B:
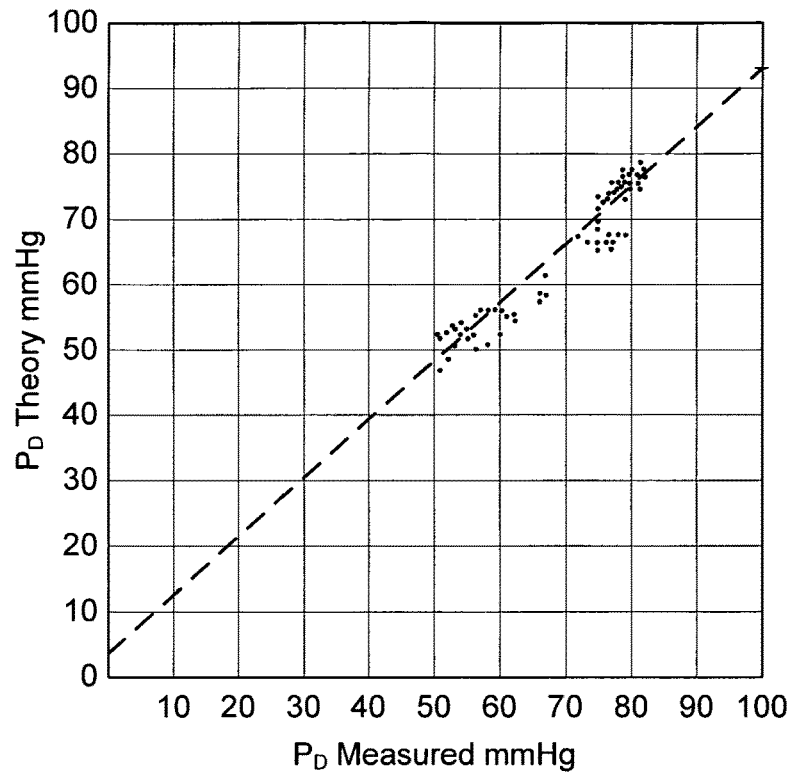
FIGS. 3B and 3C show corresponding experimental data.
Figure 3C:
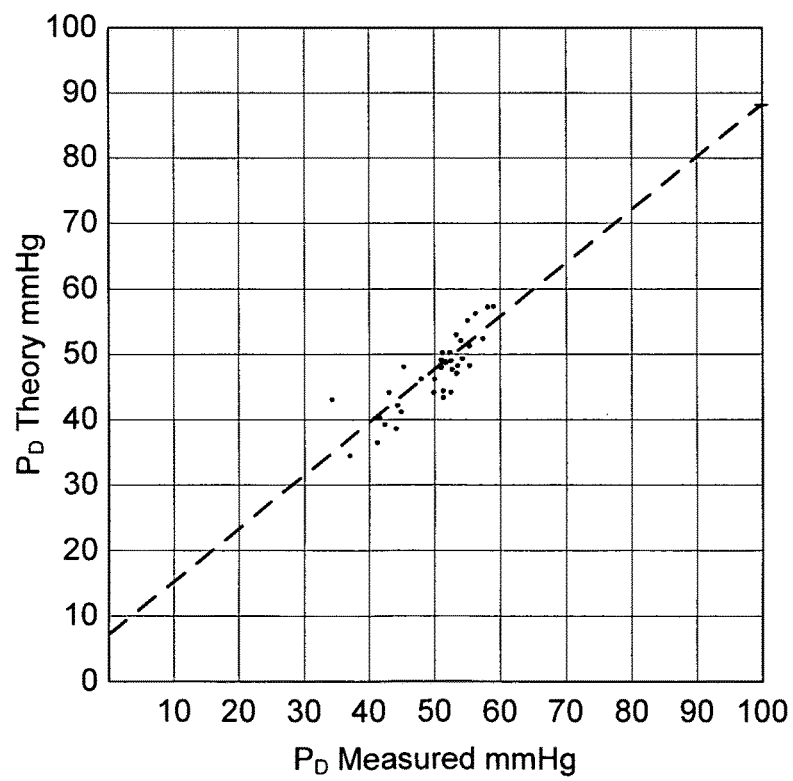

FIGS. 3B and C show $P_D$ calculated from the measured data against the measured value of $P_D$ for Experiment 1 and Experiment 2, respectively. Straight line fits to the displayed data have slopes of 0.885 and 0.795, intercepts of 3.04 mmHg and 7.31 mmHg and correlation co-efficients of 0.962 and 0.836, respectively.

Figure 4:
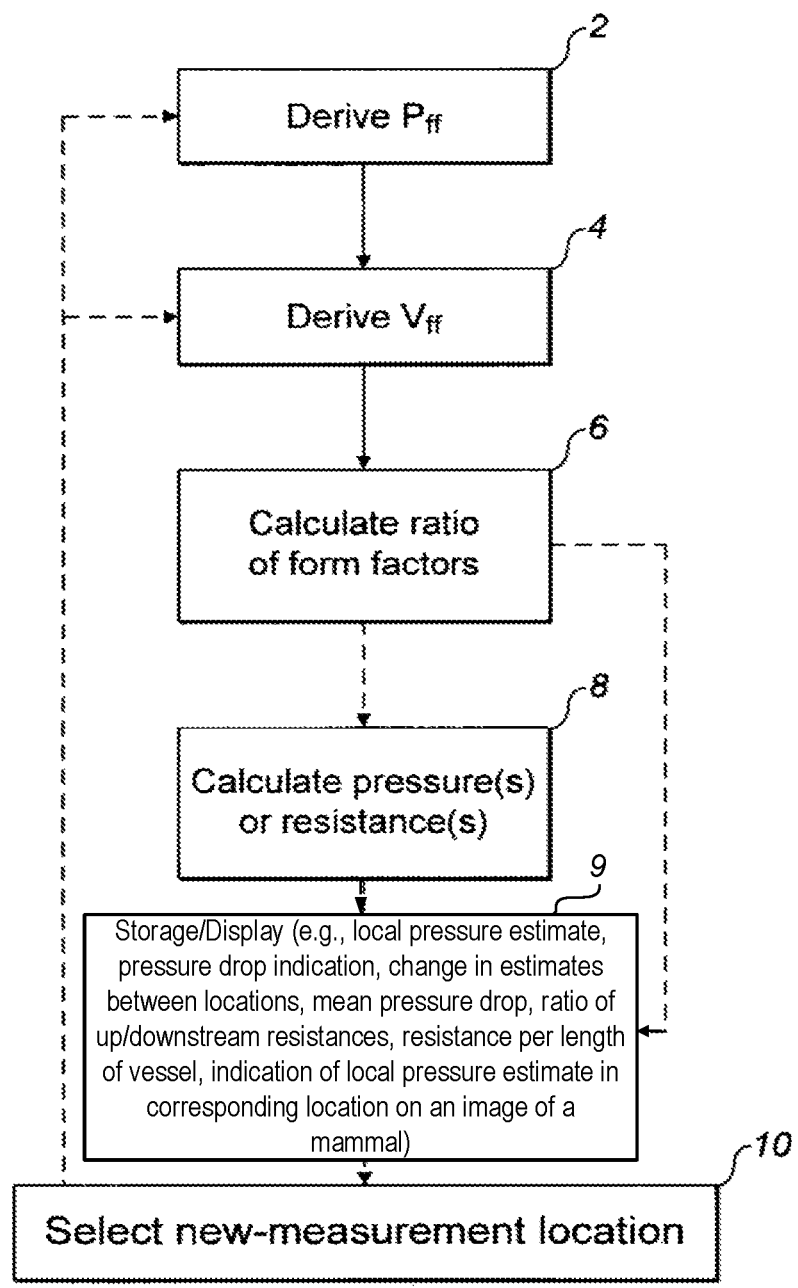
FIG. 4 is a flow diagram illustrating steps of described embodiments.

With reference to FIG. 4, a method of detecting lesions and/or estimating peripheral pressures and peripheral resistance based on the above-discussion is now described. At a first step 2, $P_{ff}$ is derived. Central Systolic Pressure (SP) and Mean Arterial Pressure (MAP) are measured or estimated. In some embodiments, a brachial cuff and sphygomomanometer is used to measure SP and the DP. The sphygomomanometer can either be of the manual variety relying on ascultation or of a known automated electronic variety. MAP can then be estimated as (2DP+SP)/3, as is well known in the art. Alternatively, where a MAP calculating electronic sphygomomanometer is used, MAP may be obtained directly from this device. Central mean pressure is assumed to be equal to MAP. From this data $P_{ff}$ can then be calculated as:—

$P_{ff}$=(SP−DP)/MAP=3(SP−DP)/(SP+2DP).

Subsequently or at the same time, $V_{ff}$ is derived. The instantaneous peripheral blood flow rate of velocity is sampled as a function of time in the artery supplying the vascular bed or tissue under investigation at step 4 and $V_{ff}$ is estimated as the difference between the maximum and minimum values of the measured waveform during a heart beat divided by the average value of the waveform.

At step 6, the ratio of form factors $P_{ff}/V_{ff}$ (or, as the case may be, $V_{ff}/P_{ff}$) is calculated as an analysis variable. This ratio corresponds to $R_S/R_L$ ($R_L/R_S$) in the above model.

At an optional step 8, pressures such as $P_D$ (the pressure at the measurement point), $P_C$−$P_D$ (the pressure drop upstream of the measurement point) or resistances such as $R_L$ or $R_S$ can be calculated. The calculation of resistances requires the availability of an average flow rate (in some embodiments calculated from flow rate waveforms by averaging over one or more heartbeats) to calculate the resistance by dividing the corresponding pressure drop by the average flow rate.

In some embodiments, the calculated values from step 8 (or step 6) are then output at step 9 for storage and/or display, as described in more detail below.

In some embodiments, stenosis or lesions are detected by scanning measurement points along a body part or vascular segment under investigation and detecting changes in $V_{ff}$, $V_{ff}/P_{ff}$, $P_{ff}/V_{ff}$, the calculated pressures or resistances or any suitable measure derived from these quantities. In these embodiments, a new measurement point is selected (e.g. by moving an ultrasound probe to a new location) following step 9 (storage and/or display of previously calculated values) and the procedure is restarted at step 2 (or step 4 if $P_{ff}$ is not recalculated). A lesion is detected, in these embodiments, by comparing the stored values and detecting a marked step-like change or difference between adjacent values. The resistance of the lesion can be derived from the magnitude of a step change in measured resistance ($R_S$ or $R_L$) between a sample point just before the lesion and a sample point just after the lesion.

In the theoretical model discussed above, $R_L$ can be seen as the resistance of the vascular bed immediately down stream from the point where the velocity or flow waveforms have been measured, including the venous return back to the right side of the heart. $R_S$ can be seen as the resistance of the arterial pathway supplying the vascular bed from the left side of the heart to the point of measurement.

By sampling at various points along the supply pathway the presence of a lesion between the last two sampling points will be signalled by an abrupt change in the computed pressures, resistances or ratios (of form factors or resistances). The precise location of the lesion may be pinpointed by moving the sample volume in small increments or a smart sampling strategy may be used to home in on the lesion. The resistance of the lesion can be established by sampling $P_D$ immediately upstream and downstream of the lesion to determine the pressure drop across the lesion (and hence its resistance given an average flow rate). This could be accomplished using Duplex ultrasound technology. Alternatively any number of lesions could be displayed in their correct anatomical location using MRI based whole body mapping device or an ultrasound mapping device (both mapping devices are described below). In accordance with the model discussed above when the sampled volume is moved from upstream to downstream of a lesion within the arterial supply pathway $P_D$ and $R_L$ drop markedly and $P_C$−$P_D$ and $R_S$ rises markedly. Similarly, $R_S/R_L$ rises markedly and from the considerations above, it is clear that $P_{FF}/V_{FF}$ can be used directly as a measure of $R_S/R_L$.

Absolute resistance measurements are relatively independent of bloodflow and allow the significance of any one lesion to be established in the case where multiple lesions are present in the same arterial pathway. In addition the magnitude of any flow rate dependency can be established with resistance measurements made during hyperaemia induced by cuff occlusion or by exercising the vascular bed. The effect on peak flow of the removal of a specific lesion or lesions may therefore be predicted.

In some embodiments, where only a single measurement is taken, an abnormally high value of $R_S$ (or $P_C$–$P_D$) indicates a lesion or stenosis upstream and an abnormally high value or $R_L$ (or $P_D$) indicates a lesion or stenosis downstream of the measurement point.

One specific application of $P_D$ would be the ability to establish the presence, due to disease, of critically low perfusion pressures in isolated organs (typically less than 30 mmHg).

Historically, ankle/brachial pressure index (ABPI) has been used as a convenient indicator of clinically significant peripheral arterial disease in the lower limbs. Systolic pressure can be simply obtained by placing a CW Doppler device over the artery immediately downstream of an encompassing pressure cuff. When the cuff is inflated to equal or just exceeds the systolic blood pressure within the artery, the audio signal from the Doppler device will cease. By recording the cuff pressure at that precise moment, the intra arterial systolic pressure is assumed to be equal the cuff pressure. An arm and an ankle blood pressure cuff are applied. In the presence of one or more clinically significant lesions within the arteries supplying the lower limbs, the ratio between ankle/arm systolic pressures falls below a preestablished threshold value. This measurement is typically carried out on a rested, supine subject.

With the realisation that mean pressure may be used in place of systolic pressure such that the ratio between ankle and arm pressure may be used to signal the presence of a haemodynamically significant lesion or lesions involving the arterial blood supply to the lower limbs, the following application is suggested. The method uses mean arm blood pressure recorded using the auscultation methods described above, from which Pff may be calculated. With Pff known, ankle pressure can be estimated (for instance), from CW Doppler blood velocity spectral waveforms obtained from the posterior tibial artery. By employing the theory described above, the calf pressure cuff is eliminated, and an analogous diagnostic ratio (ABPIm) is computed such that:—

$$ABPIm = Ankle\ mean/Brachial\ mean\ pressure = P_d/P_c = 1/(1 + P_{ff}/V_{ff})$$

The resulting ratio may be compared with a preestablished threshold. This alternative diagnostic method offers several advantages (for instance), by avoiding measurement problems caused by artificial elevation of ankle cuff systolic pressures in diabetic subjects and allowing an assessment to be made where open wounds, medical dressings or a plaster cast prevents the application of an ankle pressure cuff.

Some embodiments are arranged to estimate one or more of the parameters described above, in particular $R_S$ and $R_L$, to monitor the response of a healthy vascular system to stimuli such as drug infusion, over breathing, $CO_2$, $O_2$, respiratory disease, cardiac failure, ambient temperature, digestion or mental arithmetic.

Figure 5:
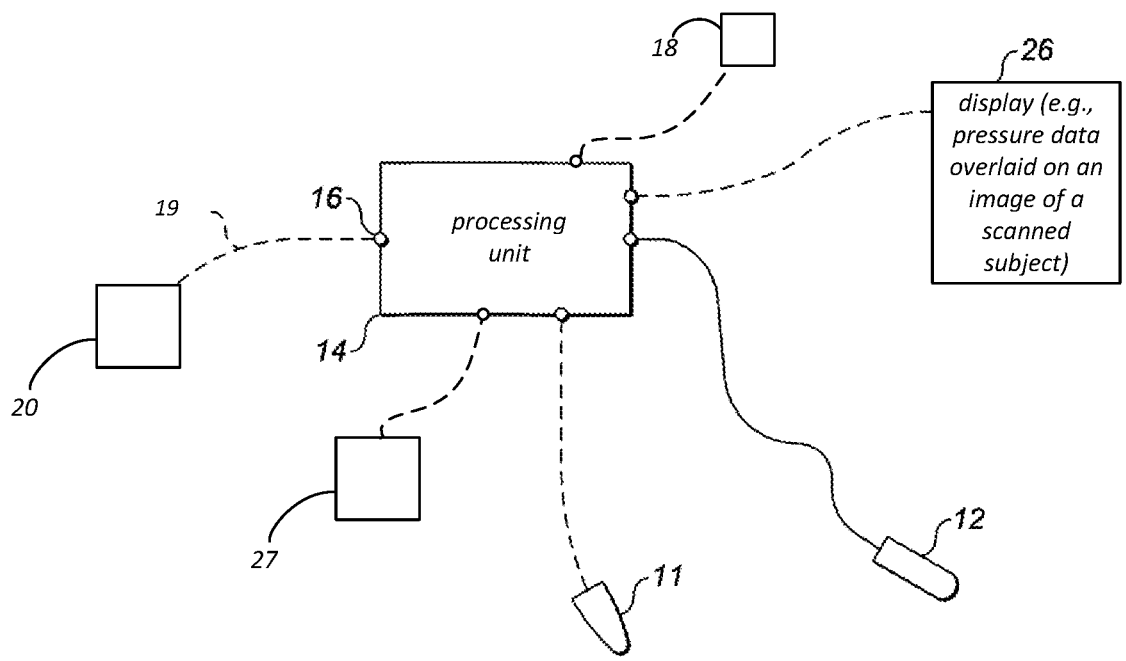
FIG. 5 illustrates ultrasound-based embodiments.

Various embodiments which use different modalities to measure velocity of flow waveforms and different arrangements for the display of pressure and/or resistance data are now described. With reference to FIG. 5, some embodiments include a Continuous Wave (CW) Doppler ultrasound probe 12 connected to a processing unit 14. The processing unit 14 includes an input device such as a keyboard 18 and a display device such as a LCD screen 26. In some embodiments, the processing unit may be a portable computer such as a tablet PC to which the probe 12 is connected via an appropriate control card. The probe 12 is used to sample velocity waveforms over a tissue to be analysed which is then processed by the processing unit 14 to extract $V_{ff}$, as described above. $P_{ff}$ and the central mean pressure may be calculated manually or by a separate device as described below and then entered into the processing unit 14, for example using a keyboard 18. Alternatively, measurements of SP and DP are entered using the keyboard or otherwise, with the processing unit 14 calculating $P_{ff}$ and MAP from the entered date. A value for the mean distal pressure is then calculated as described above by the processing unit 14 and output on the display 26. In some embodiments, the output takes a form of a numerical or graphical display of the estimated value on the display.

The location of a stenosis can be determined by scanning the probe 12 along the vascular segment under investigation. This is analogous to, in the electrical equivalent, measuring the voltage variation of the middle terminal of a potentiometer as the potentiometer setting is changed. By moving the probe along the vascular segment and continuously or repeatedly calculating one or more of the measures discussed above, the location of stenosis can be indicated by a change of the measure or measures), as discussed above, once the lesion has been traversed by the probe.

Figure 6:
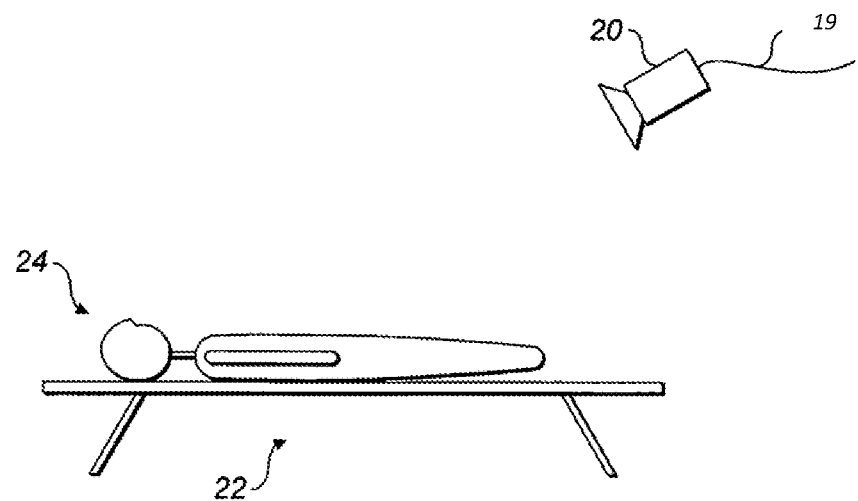
FIG. 6 illustrates non invasive ultrasound-based embodiments enabling the overlay of estimated pressure, resistance or linear resistance data obtained at multiple locations over a video image of a subject.

In some embodiments, the processing unit 14 has an input 16 providing an optional connection 19 to an image capture device 20 described below with reference to FIG. 6. The image capture device 20 is installed relative to a patient bed 22 to obtain an image of all or part of a patient 24 to allow the distal pressure measurements to be correlated with the region of the patient's body where the flow data has been measured. In some embodiments, an operator is prompted by the display of the processing unit 14 to obtain data at a given location by a visual indication such as a cross hair on the video image of the patient so that a visual map of peripheral pressures may be build up scanning location by scanning location. In some embodiments, the process is further automated in that the image capture device 20 comprises an arrangement for tracking the position of the probe 12 on the video image so that the measurement location can be correlated automatically with the image. To facilitate tracking of the probe, an electromagnetic transmitter or optical marker is secured to the tip of the probe 12 in some embodiments. The location of the marker when the measurement is taken is obtained either from the video image itself in some embodiments or from a 3D tracking device using passive or active, optical or electromagnetic, for example infrared or radio-frequency, markers, such as an OptoTrack® or Polhemus® device in some embodiments.

Once captured, the calculated pressure data is displayed on a display device of the processing unit 14 at the location on the image where the velocity waveform was sampled, for example as a colour coded false-colour display where a track or image representing the path of the underlying blood vessel is overlaid on an image of the scanned subject. Track colour is dependent on the local computed variable (for instance), the value of $P_D$. The computed pressure data can also be stored together with location data and the video image for later display and/or processing. Some embodiments provide a further optional feature of displaying a velocity spectrum obtained from the Doppler probe registered with the image, for example by placing respective expandable thumbnail images on the image at corresponding measurement locations.

In some embodiments, capturing of the central mean pressure and $P_{ff}$ data is automated by appropriately connecting an electronic sphygmomanometer 27, for example using a brachial cuff to the processing unit 14 so that the respective measurements of these quantities can be updated automatically and periodically as measurements with the ultrasound probe 12 are obtained.

In some embodiments, the processing unit 14 and ultrasound probe 12 are replaced with a Duplex ultrasound scanning system which may, in some embodiments be operated in an equivalent fashion to the CW Doppler embodiments described above, that is the system includes a corresponding processing unit 14 and duplex probe 12 together with the optional input 16 and the optional electronic sphygmomanometer 27. Given the capability to image a two dimensional cross section through blood vessels, the duplex ultrasound system has the additional functionality of calculating flow rate waveforms in additions to velocity waveforms. In some embodiments the flow rate data is used to calculate and display the absolute values of Rs and $R_L$ and/or the resistance per unit length of the blood vessel (linear resistance) as described above.

In some embodiments an optional Multi Gate Doppler 11 is used to measure the blood flow and velocity profile concurrently with data from CW Doppler 12. Velocity profile and linear resistance are processed in processing unit 14 to yield instantaneous blood viscosity versus shear data (pointwise rheological measurement) which can be displayed on screen 26. (See 'Online viscosity measurement of complex solutions using Ultrasound Doppler Velocimetry', Koseli V, Zeybek S and Uludag Y: Turk J Chem 30 (2006), 297-305 herewith incorporated by reference herein).

Figure 7:
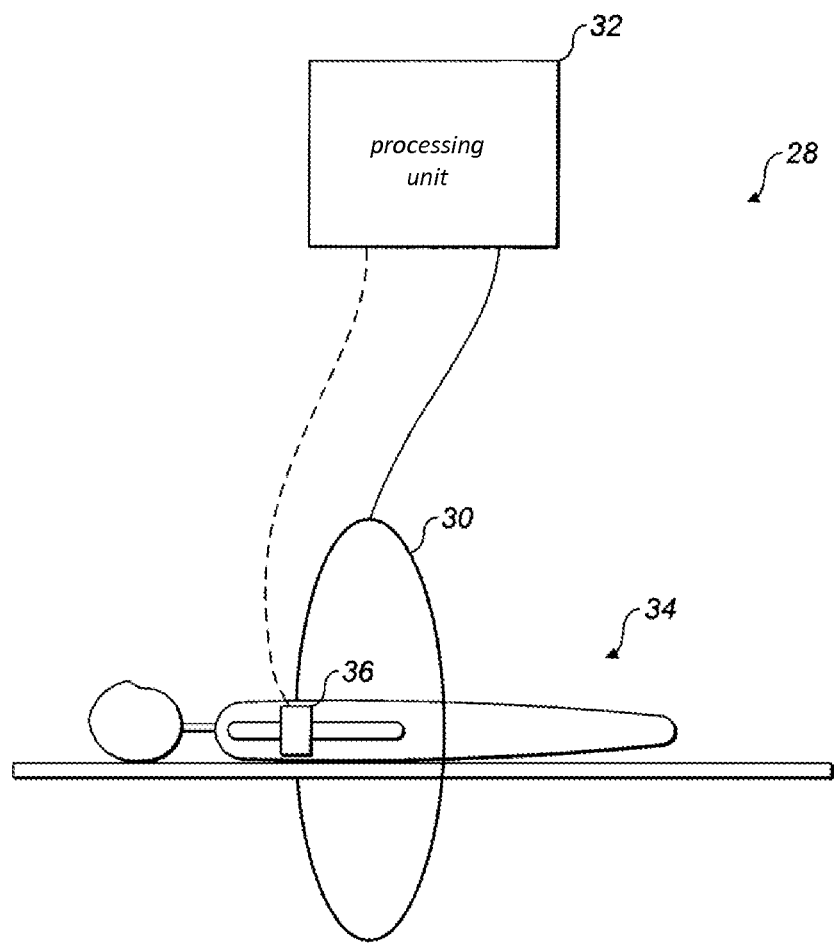
FIG. 7 illustrates an MRI-based embodiment which enables the overlay of estimated pressure, resistance or linear resistance data obtained at multiple locations over a whole body image of the subject.

With reference to FIG. 7, in some embodiments, velocity and/or flow measurements are obtained using a MRI system 28 comprising a RF coil system schematically depicted at reference numeral 30 and a processing unit 32 which controls the RF coil system 32 to allow read-out of both anatomical, vascular and velocity/time or flow/time data at specified vascular sites of a patient 34 placed in the coil system 30, as is well known in the art. For each voxel or group of voxels where a velocity or flow value is calculated by the processing unit 32 a corresponding pressure and/or resistance value is derived by the processing unit 32 using the method described above. $P_{\!f\!f}$ is calculated from manually entered data in some embodiments and obtained automatically, for example using a brachial cuff 36, in others. Thus, a voxel map of pressure and/or resistance or one or more of the measures discussed above is calculated and stored by the processing unit 32 and can be used to colour code a voxel image of a scanned vascular location by pressure and/or resistance or to identify a segment of the vascular system in which, for example, hydraulic resistance exceeds a particular value. Again, the location of a stenosis can be indicated by an abnormal step change of one or more of the measures described above.

Figure 8:
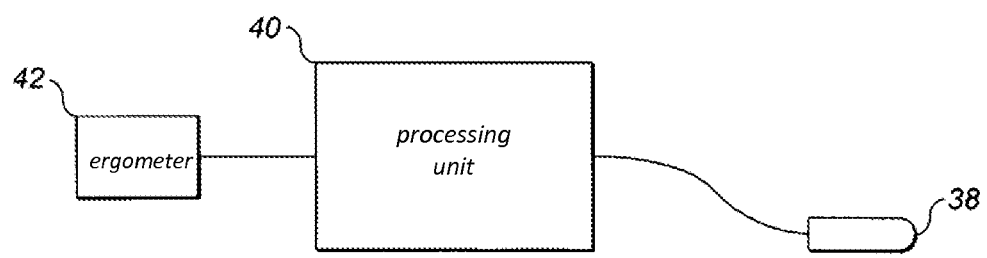
FIG. 8 illustrates a system for estimating maximum energy output of a subject.

In some embodiments, now described with reference to FIG. 8, an ultrasound probe 38, for example a CW Doppler ultrasound probe is connected to a processing unit 40, which in return receives an input from an ergometer 42 providing a measured value of work rate as an athlete or patient exercises on the ergometer. It has previously been shown (see Post Exercise Blood Velocity Patterns in Health and Disease, King D H, Bojanowski L M R, Di Giovanna I, and Kontis S. in Computer-aided biomedical imaging and graphics, physiological measurement and control: Proceedings of the Biological Engineering Society $6^{th}$ Nordic Meeting, Aberdeen, 22-25 Jul. 1984 ed M M Jordan and W J Perkins, incorporated herein by reference) that at maximal vasodilation in claudicants, following unilateral calf muscle exercise until forced to stop due to calf pain or discomfort, the vascular bed defaults to the matched state in which $P_{\!f\!f}/V_{\!f\!f}=1$. This is the point at which maximum hydraulic power is dissipated in the vascular bed. By monitoring and displaying the ratio $P_{\!f\!f}/V_{\!f\!f}$ using the probe 38 and the processing unit 40 as a patient or athlete exercises on the ergometer, work rate data received from the ergometer 42 by the processing unit 40 when the matched state of $P_{\!f\!f}/V_{\!f\!f}=1$ (or, as an approximation, $V_{\!f\!f}$ being within a defined margin of $P_{\!f\!f}$) is displayed and recorded as a measure of individual best performance. In some embodiments, a signal indicating the matched state is generated and triggers recording of the work rate data. This can be used to help athletes monitor training progress and also to allow patients such as claudicants to establish their maximum walking exercise capability and monitor any improvement due to medication or exercise.

It will be understood that the above description is made by way of example only and of embodiments of the invention to further the understanding of the invention and is not intended to be limiting. Many modifications, variations, combinations and juxtapositions of the embodiments described above will be apparent to a person skilled in the art and are intended to be covered by the scope of the appended claims.

Although mean central pressure and $P_{\!f\!f}$ measurements have been described above in relation to a brachial cuff sphygmomanometer 27 a number of alternative techniques can equally be used. For example a servo finger pressure follower such as a Finapress® sensor, could be used to measure SP and DP. A further method for measuring $P_{\!f\!f}$ is to provide a total occlusion just downstream of the location to be measured and to then to measure pulse pressure (SP-DP) and MAP immediately upstream of the total occlusion, for example using a pressure follower or by a calibrated tonometric device placed over the peripheral artery just upstream of the total occlusion. The total occlusion, for example by tourniquet, provides a reflective antinode for the incident pressure wave such that the pulse pressure is double its zero reflection (matched) value. In this way, by providing a reflection of known amplitude (total constructive reflection) the effect of otherwise unknown reflections in the artery can be eliminated and an estimate of $P_{\!f\!f}$ can be obtained as $P_{\!f\!f}$=pulse pressure/(2*mean pressure). (see 'An in vivo study of the total occlusion method for the analysis of forward and backwards pressure waves' D L Newman, S E Greenwald and N L R Bowden; Cardiovascular Research 1979 13(10): 595-600 herewith incorporated by reference herein).

A method which allows computation of the entire scaled incident pressure/time waveform is now described, based on the demonstrated tendency for the periphery to default to the matched state $P_{\!f\!f}=V_{\!f\!f}$ when under stress or heavy load (see Post Exercise Blood Velocity Patterns in Health and Disease, King D H, Bojanowski L M R, Di Giovanna I, and Kontis S. in Computer-aided biomedical imaging and graphics, physiological measurement and control: Proceedings of the Biological Engineering Society $6^{th}$ Nordic Meeting, Aberdeen, 22-25 Jul. 1984 ed MM Jordan and WJ Perkins) The method comprises constricting the brachial artery in the upper arm for 5 minutes by means of an suprasystolic inflated pressure cuff, followed by recording the hyperaemic brachial artery blood velocity/time waveform for a period of several heartbeats immediately following release of the cuff. Because the distal vascular bed including the forearm muscles and the tissues in the hand will vasodilate maximally in order to restore the oxygen debt built up during the period of cuff constriction, the waveform recorded during the first few seconds of vasodilation will approximate the incident pressure waveform arising from the left ventricle and can be scaled to its absolute pressure/time equivalent if it's mean value is set equal to the value of mean arterial pressure obtained by the methods described previously.

The data obtained by this method, in some embodiments, is used to validate and/or calibrate estimates of $P_{ff}$ obtained using, for example, a simple brachial cuff measurement as described above. Alternative means for achieving maximal vasodilation may be employed (for instance), repetitive exercise of the downstream muscle bed (forearm) whilst sampling brachial artery blood velocity/time waveform or alternatively (for instance) exercising the hand using a repetitive squeezing action whilst sampling radial artery blood velocity/time waveforms. These methods can be used in order to achieve a more accurate estimate of Pff compared with conventional auscultation or in order to confirm the accuracy of the conventional auscultation method.

A further, albeit invasive, option is to insert a balloon catheter with an upstream pressure sensor in the measurement location, to inflate the balloon catheter to obtain the total occlusion and then to proceed as outlined above. This method can also be used where the pressure wave does not originate from the left ventricle, for example in pulmonary artery arising from the right ventricle.

Likewise, any other instantaneous flow or velocity measurement technique can be used in place of those described above. Any other sensing technique for recording a localised instantaneous flow/time or velocity/time waveforms can equally be employed.

The above derivation is based on the realisation that a ratio of measures indicative of shape of central blood pressure and local blood velocity of flow waveforms can be used to replace the ratio of resistances in the standard haemodynamic pressure divider equation. The above discussion has been centred on the particular example of a Form Factor index, as defined above. However, other measures are equally envisaged to be used in place of the Form Factor used in the described embodiments, as will be apparent to the skilled person. Such measures may include the Fourier coefficient of the first component of a normalised Fourier transform of the waveforms or any other measure of determining the shape of the waveforms, specifically those which are indicative of the relative contribution of the AC and DC components of the waveforms.

The invention claimed is:

1. A system, including:
   a non-invasive blood flow measurement device;
   a display device; and
   a processing device, in communication with the non-invasive blood flow measurement device and with the display device, configured to:
      receive blood flow data, generated by the blood flow measurement device, wherein the blood flow data includes a velocity waveform of blood flow at a location in a segment of a vascular system of a mammal, or the blood flow data includes a flow rate waveform of blood flow at the location in the segment of the vascular system of the mammal;
      receive a central mean pressure of the mammal;
      determine a first measure of a shape of the blood flow data and store the first measure in a storage device in association with the corresponding location, wherein the first measure represents a ratio between (1) a difference between a maximum magnitude of the blood flow data and a minimum magnitude of the blood flow data and (2) an average magnitude of the blood flow data;
      generate a local pressure estimate by division of the central mean pressure by a sum of (1) unity and (2) a ratio of a second measure to the first measure, wherein the second measure represents a ratio between (1) a difference between a maximum magnitude of a central pressure waveform and a minimum magnitude of the central pressure waveform and (2) the central mean pressure; and
      cause the display device to display a visual representation of the local pressure estimate.

2. A system as claimed in claim 1, further including a pressure measurement device, communicatively coupled to the processing device, to sense the central pressure waveform.

3. A system as claimed in claim 1, wherein receive the central mean pressure of the mammal includes:
   receive a systolic pressure to provide the maximum magnitude of the blood flow data and a diastolic pressure to provide the minimum magnitude of the blood flow data; and
   determine the central mean pressure of the mammal based on the systolic and diastolic pressures.

4. A system as claimed in claim 1, wherein the blood flow measurement device includes a Doppler ultrasound system.

5. A system as claimed in claim 1, further including an image capture device for capturing an image of at least part of the mammal, wherein the processing device is coupled to the image capture device and is further configured to register a location of the blood flow measurement device on the mammal with an image generated by the image capture device.

6. A system as claimed in claim 5, wherein the blood flow measurement device includes an electromagnetic or visual marker adjacent to a sensing end of the blood flow measurement device.

7. A system as claimed in claim 5, wherein the processing device is to cause the display, on the display device, of the local pressure estimate on an image of the mammal at a corresponding location in the image.

8. A system as claimed in claim 1, wherein the blood flow measurement device includes a magnetic resonance system.

9. A system as claimed in claim 1, wherein the processing device is further configured to generate an absolute mean pressure estimate or an estimate of a drop of mean pressure along the segment of the vascular system.

10. A system as claimed in claim 1, wherein the processing device is further configured to generate a resistance estimate based on a pressure drop along the vascular segment and on an absolute local blood flow measurement within the vascular segment.

11. A system as claimed in claim 1, wherein the processing device is further configured to:
   receive a plurality of sets of blood flow data taken at a corresponding plurality of locations in the segment;
   for each set of blood flow data, calculate a first measure of a shape of the blood flow data and store the calculated first measure in a storage device in association with the corresponding location;
   for each location, compare the corresponding first measure and the second measure to generate a local pressure estimate; and
   cause the display, on the display device, of a visual representation of a change in the local pressure estimates between locations, signifying presence of a lesion.

12. A system as claimed in claim 11, wherein the processing device is to cause the display, on the display device, of a visual representation of a drop in mean pressure, a ratio of resistances upstream and downstream of a measurement location, or a resistance per unit length of blood vessel.

13. A system as claimed in claim 1, wherein the processing device is further configured to generate, based on the local pressure estimate, a resistance estimate, a resistance per unit length of blood vessel, or a measure of blood viscosity.

14. A system as claimed in claim 1, wherein the processing device is configured to receive, via an input device, a systolic pressure to provide the maximum magnitude of the central pressure waveform and a diastolic pressure to provide the minimum magnitude of the central pressure waveform.

15. A system as claimed in claim 14, wherein receive the central mean pressure includes:
receive, via the input device, the central mean pressure.

16. A system as claimed in claim 1, further including a pressure measurement device, communicatively coupled to the processing device, to generate blood pressure data.

17. A system as claimed in claim 1, wherein the visual representation includes a value of the local pressure estimate.

18. A system as claimed in claim 1, wherein the processing device is to cause the display device to display an indication of a pressure drop.

19. A system as claimed in claim 1, wherein the processing device is included in a personal computing device.

20. A system as claimed in claim 19, wherein the processing device is included in a tablet computing device.

21. A system as claimed in claim 1, wherein the processing device is further to receive the maximum magnitude of the central pressure waveform and the minimum magnitude of the central pressure waveform via an input device.

22. A system as claimed in claim 21, wherein the input device includes a keyboard.

23. A system as claimed in claim 1, wherein the display device and the processing device are part of a common processing unit.

24. A system as claimed in claim 23, wherein the processing unit is a tablet.

25. One or more non-transitory computer readable media having instructions thereon that, in response to execution by one or more processing devices of an apparatus, cause the apparatus to:
receive blood flow data, generated by a blood flow measurement device, wherein the blood flow data is a velocity waveform of blood flow at a location in a segment of a vascular system or a flow rate waveform of blood flow at the location in the segment of the vascular system;
determine a first measure of a shape of the blood flow data and store the first measure in a storage device in association with the corresponding location, wherein the first measure represents a ratio between (1) a difference between a maximum magnitude of the blood flow data and a minimum magnitude of the blood flow data and (2) an average magnitude of the blood flow data;
receive a central mean pressure of the vascular system;
generate a local pressure estimate by division of the central mean pressure by a sum of (1) unity and (2) a ratio of a second measure to the first measure, wherein the second measure represents a ratio between (1) a difference between a maximum magnitude of a central pressure waveform and a minimum magnitude of the central pressure waveform and (2) the central mean pressure; and
cause a display device to display a visual representation of the local pressure estimate.

26. One or more non-transitory computer readable media as claimed in claim 25, wherein the central mean pressure includes systolic and diastolic pressures, and wherein the one or more non-transitory computer readable media further has instructions thereon that, in response to execution by the one or more processing devices of the apparatus, cause the apparatus to estimate the central mean pressure based on the systolic and diastolic pressures.

27. One or more non-transitory computer readable media as claimed in claim 25, wherein the visual representation of the local pressure estimate includes a value of the local pressure estimate.

28. One or more non-transitory computer readable media as claimed in claim 25, wherein the visual representation of the local pressure estimate includes an indication of a pressure drop.

29. One or more non-transitory computer readable media as claimed in claim 25, wherein the apparatus is a tablet computing device.

30. A method of performing monitoring of a patient, comprising:
receiving, by a processing apparatus, blood flow data, generated by a blood flow measurement device, wherein the blood flow data is a velocity waveform of blood flow at a location in a segment of a vascular system or a flow rate waveform of blood flow at the location in the segment of the vascular system;
determining, by the processing apparatus, a first measure of a shape of the blood flow data and store the first measure in a storage device in association with the corresponding location, wherein the first measure represents a ratio between (1) a difference between a maximum magnitude of the blood flow data and a minimum magnitude of the blood flow data and (2) an average magnitude of the blood flow data;
receiving, by the processing apparatus, a central mean pressure of the vascular system of the patient;
generating, by the processing apparatus, a local pressure estimate by division of the central mean pressure by a sum of (1) unity and (2) a ratio of a second measure to the first measure, wherein the second measure represents a ratio between (1) a difference between a maximum magnitude of a central pressure waveform and a minimum magnitude of the central pressure waveform and (2) the central mean pressure; and
causing, by the processing apparatus, a display device to display a visual representation of the local pressure estimate.

31. A patient monitoring system, including:
a non-invasive blood flow measurement device;
a display device; and
a processing device, in communication with the non-invasive blood flow measurement device and with the display device, configured to:
receive blood flow data, generated by the blood flow measurement device, wherein the blood flow data includes a velocity waveform of blood flow at a location in a segment of a vascular system of a patient, or the blood flow data includes a flow rate waveform of blood flow at the location in the segment of the vascular system of the patient;

determine a first measure of a shape of the blood flow data, wherein the first measure represents a ratio between (1) a difference between a maximum magnitude of the blood flow data and a minimum magnitude of the blood flow data and (2) an average magnitude of the blood flow data;

generate a local pressure estimate by division of a central mean pressure by a sum of (1) unity and (2) a ratio of a second measure to the first measure, wherein the second measure represents a ratio between (1) a difference between a maximum magnitude of a central pressure waveform and a minimum magnitude of the central pressure waveform and (2) the central mean pressure; and cause the display device to display the local pressure estimate.

* * * * *